United States Patent
Tomatis

(10) Patent No.: US 7,192,613 B2
(45) Date of Patent: Mar. 20, 2007

(54) *ALLIUM SATIVUM* BULB ABSOLUTES AND THERAPEUTIC OR COSMETIC USES

(75) Inventor: Isabelle Tomatis, Tounefeuille (FR)

(73) Assignee: Pierre Fabre Dermo-Cosmetique, Boulogne Billancourt (FR)

( * ) Notice: Subject to any disclaimer, the term of this patent is extended or adjusted under 35 U.S.C. 154(b) by 270 days.

(21) Appl. No.: 10/493,549

(22) PCT Filed: Oct. 22, 2002

(86) PCT No.: PCT/FR02/03618

§ 371 (c)(1),
(2), (4) Date: Apr. 22, 2004

(87) PCT Pub. No.: WO03/035085

PCT Pub. Date: May 1, 2003

(65) Prior Publication Data
US 2004/0258777 A1 Dec. 23, 2004

(30) Foreign Application Priority Data
Oct. 26, 2001 (FR) .................................. 01 13839

(51) Int. Cl.
*A61K 36/00* (2006.01)
(52) U.S. Cl. ...................................... 424/754; 424/725
(58) Field of Classification Search ................ 424/754, 424/725
See application file for complete search history.

(56) References Cited
U.S. PATENT DOCUMENTS
2002/0146474 A1 10/2002 Tomatis

FOREIGN PATENT DOCUMENTS

| EP | 0 464 521 | 1/1992 |
|---|---|---|
| JP | 4-338336 | 11/1992 |
| WO | 02/36093 | 5/2002 |

OTHER PUBLICATIONS

Database WPI Section Ch, Week 198612 Derwent Publications Ltd. London, GB; AN 1986-078768 XP002206274 & JP 61 027910 A (Kao Corp.), Feb. 7, 1986, Abstract only.

Database Biosis 'en ligne! Biosciences Information Service, Phildelphia, PA, US; Apr. 1998 Bordia et al.: "Effect of garlic (*Allium sativum*) on blood lipids, blood sugar, fibrinogen and fibrinolytic activity in patients with coronary artery disease." Database accession No. PREV199800315438 XP002206271 abrege & *Prostaglandins leukotrienes* and Essential Fatty Acids, vol. 58, No. 4, Apr. 1998 pp. 257-263, ISSN: 0952-3278, Abstract only.

Database FSTA 'en ligne! International Food Information Service (IFIS), Frankfurt/Main, DE; Hwang S et al.: "Studies on processing techniques of garlic (*Allium sativum*, Linn.)." Database accession No. 83-2-09-t0517 XP002206272 abrege & Research Bulletin of Tainan District Agricultural Improvement Station 1982 Hort. Sect., Tainan District Agric. Improvement Sta., Tainan City, Taiwan, Abstract only.

(Continued)

*Primary Examiner*—Christopher Tate
*Assistant Examiner*—S. B. McCormick-Ewoldt
(74) *Attorney, Agent, or Firm*—Young & Thompson

(57) ABSTRACT

The invention concerns *Allium* sativum bulb absolutes, compositions containing them, and uses thereof for therapeutic purposes—in particular in the treatment of obesity—and for cosmetic purposes—in particular for the treatment of the skin, of cellulite and of localized dermal adipose deposits.

22 Claims, 2 Drawing Sheets

OTHER PUBLICATIONS

Figure 1A:

Database WPI Section Ch, Week 197618 Dewent Publications Ltd., London, GB AN 1976-33191X XP002206275 & JP 51 033066 A (Mitsui Y), Mar. 19, 1976, Abstract only.

Database Biosis 'en ligne! Biosciences Information Service, Phildelphia, PA, US; Mar. 7, 2001 Mousa Ahmed S.: "Discovery of angiogenesis inhibition by garlic ingredients: Potential anti-cancer benefits." Database accession No. PREV200100255676 XP002206273 abrege & Faseb Journal, vol. 15, No. 4, Mar. 7, 2001, p. A117 Annual Meeting of the Federation of American Societies for Experimental Biology on Experimental Biology 2001; Orlando, Florida, USA; Mar. 31-Apr. 4, 2001 ISSN: 0892-6638, Abstract only.

Ferrara et al. "Molecular and Biological Properties of the Vascular Endothelial Growth Factor Family of Proteins" Endocrine Reviews, vol. 13, No. 1, 1992 pp. 18-32.

Folkman et al. "Angiogenesis" The Journal of Biological Chemistry, vol. 267, No. 16, Issue of Jun. 5, pp. 10391-10394, 1992.

Keck et al. "Vascular Permeability Factor, an Endothelial Cell Mitogen Related to PDGF" Science, vol. 246, pp. 1309-1312, Dec. 8, 1989.

Mustonen et al. "Endothelial Receptor Tyrosine Kinases Involved in Angiogenesis" The Journal of Cell Biology, vol. 129, No. 4, May 1995, pp. 895-898.

Klaus. "Functional differentiation of white and brown adipocytes," BioEssays, vol. 19, No. 3, pp. 215-223.

Morrison et al. "Insights into the Transcriptional Control of Adipocyte Differentiation," Journal of Cellular Biochemistry Supplements 32/33:59-67 (1999).

MacDougald et al. "Regulated expression of the obese gene product (leptin) in white adipose tissue and 3T3-L1 adipocytes," Proc. Natl. Acad. Sci. USA, vol. 92, pp. 9034-9037, Sep. 1995.

1  2  3  4

5  6

ALLIUM SATIVUM BULB ABSOLUTES AND THERAPEUTIC OR COSMETIC USES

The invention concerns *Allium* sativum (garlic) bulb extracts and uses thereof. Said compositions can be advantageously and more particularly used in the pharmaceutical and cosmetics industry. The invention thus also concerns therapeutic compositions (medicaments), particularly for the treatment of obesity. The invention also extends to cosmetic compositions, particularly cosmetic compositions for topical application for beauty (beauty products) or skin care, and cosmetic compositions for the preventive or curative treatment of cellulite and/or of localized dermal adipose deposits by topical application.

Throughout the text, the terms defining the extraction products (essential oil, concrete, oleoresin or resinoid, absolute, etc.) are used in accordance with the terminology defined by the standard NF T 75-006 (February 1998).

*Allium* sativum, or garlic, has long been known for its nutritional value (high content of proteins, vitamins A and C, thiamin and mineral salts), for its digestive benefits, and for its antiseptic, antiviral, cardio-protective, tonic and diuretic action, etc. However, because of its characteristic strong odor, it is not greatly appreciated except in small quantities for culinary preparations.

Also, in contrast to other plants that have formed the subject of a wide range of extracts: essential oils, concretes, oleoresins, absolutes, etc., publications mentioning extracts based on *Allium* sativum are rare. JP-04 338 336, for example, describes tablets for the oral treatment of obesity containing an extract of garlic obtained from dried garlic extracted once with water or ethanol. This is thus an oleoresin extract.

The present invention thus sets out to fill this gap by providing new compositions, in particular new water-soluble garlic extracts, whose properties can be advantageously used by industry, particularly in the pharmaceutical industry or in the cosmetics industry, and which can be obtained by a process that is both simple and inexpensive to implement.

The invention also aims to provide uses for these compositions, particularly for the therapeutic treatment of obesity, or for the topical cosmetic treatment of the skin, of cellulite and/or of localized dermal adipose deposits.

The invention thus concerns an *Allium* sativum bulb absolute.

An absolute is an extract resulting from at least two extraction stages. The first stage is carried out with a volatile non-aqueous—in particular non-aromatic—extraction solvent and produces a concrete or an oleoresin. The second stage is carried out with ethanol as solvent. It should be noted that plant absolutes display a very concentrated odor which is characteristic of the plant. They are conventionally prepared and used exclusively in the perfume industry. In addition, there was no interest in an absolute produced from garlic, whose odor lends itself so little to this category of extract. In addition, until now nothing in current knowledge has related to absolutes obtained from *Allium* sativum bulbs.

Although JP 51 033066, EP 0 464 521, FR 01/03325 describe garlic extracts, none of them describes an *Allium* sativum bulb absolute according to the invention, nor a process for obtaining an absolute, nor an extract that has the structural or functional characteristics of an absolute.

The *Allium* sativum bulb absolutes are advantageously obtained according to the invention from at least one concrete (extract of fresh or thawed garlic with a volatile non-aqueous—in particular non-aromatic —solvent), in particular a concrete extracted with hexane (throughout the text, the term ACH denotes an absolute obtained from a concrete extracted with hexane) or a concrete extracted with ethyl acetate (throughout the text, the term ACEA denotes an absolute obtained from a concrete extracted with ethyl acetate).

According to another embodiment of the invention, an *Allium* sativum bulb absolute is obtained from at least one oleoresin extract (extract of dried garlic with a volatile non-aqueous—in particular non-aromatic—solvent), in particular an oleoresin extract extracted with acetone (throughout the text, the term AOA denotes an absolute obtained from an oleoresin extracted with acetone).

The invention also concerns a process for obtaining an *Allium* sativum extract corresponding to an absolute according to the invention.

A process for obtaining an *Allium* sativum extract according to the invention comprises the following steps:
- extraction of *Allium* sativum bulbs with a volatile non-aqueous solvent,
- evaporation of the solvent to obtain a first extraction product.

According to the invention, this first extraction product then undergoes a subsequent extraction with ethanol to obtain an absolute.

It should be noted that if the plant material used is fresh or thawed material (having been frozen to preserve it), the first extraction product, obtained after the solvent extraction step, is a concrete. It is an oleoresin extract (or resinoid) if the plant material is used in the dried state for this same extraction step.

Throughout the text, the term "bulbs" encompasses both the bulbs of the plant (groups of cloves of garlic) and the individual cloves, peeled or not.

According to the invention, the plant material used in the process according to the invention is advantageously fresh or thawed material (having been frozen to preserve it).

According to the invention, the subsequent extraction with ethanol, by means of which in particular waxes can be eliminated from the first extraction product, advantageously consists in:
- dissolving the first extraction product in ethanol at ambient temperature and recovering a first ethanol solution by filtration,
- cooling the first ethanol solution to a temperature in the order of $-10°$ C. and then filtering it to recover a second ethanol solution,
- distilling the ethanol from the second ethanol solution to finally obtain an absolute.

According to the invention, the extraction stage with a volatile non-aqueous solvent is advantageously performed with a volatile non-aqueous and non-aromatic solvent.

According to the invention, this extraction is advantageously performed with hexane or ethyl acetate as volatile non-aqueous and non-aromatic solvent.

According to a variant of the invention, the plant material used in the process according to the invention is plant material in the dried state. According to the invention, the extraction is advantageously performed with acetone as volatile non-aqueous and non-aromatic solvent.

The invention also extends to a composition containing at least one *Allium* sativum bulb absolute, having particularly interesting applications, notably for therapeutic and/or cosmetic purposes.

The composition according to the invention is based on the very surprising and unexpected discovery of the effects of absolutes according to the invention at the level of two biological mechanisms of the human body: cutaneous microcirculation and the differentiation of preadipocytes to adipocytes.

At the level of cutaneous microcirculation, the inventor has demonstrated that absolutes according to the invention have a positive influence on the secretion of VEGF (vascular endothelial growth factor).

VEGF is one of the most important factors in the positive regulation of angiogenesis (Ferrera N., Endocr. Rev. 13:18-32, 1992), vasodilation (Folkman J. et al., J. Biol. Chem. 267:10931-10934, 1992), vascular permeability (Keck P. J., Science 246:1309-1312, 1989). It is specific to vascular endothelium. This is one of the most important factors in the growth and survival of endothelium. It is regarded as being the major pro-angiogenic factor. Its action is limited to the level of endothelial cells (Mustenen T. et al., J. Cell. Biol. 129:895-898, 1995) and its expression is perfectly correlated with the process of angiogenesis associated with the process of repair.

For that reason, *Allium* sativum bulb absolutes are of great interest in the manufacture of medicaments, particularly in the treatment of cutaneous disorders, where they can be advantageously used as activators of cutaneous microcirculation. They can also make an effective contribution, as auxiliary agents, to any therapeutic or cosmetic treatment (beauty product, skin treatment, etc.) in which an improvement in microcirculation is desired.

This is because the skin is highly vascular. Cutaneous circulation takes place at the level of the dermis: no blood vessels penetrate the epidermis, whose metabolic needs are met by diffusion from the papillary dermis. Cutaneous circulation is responsible for the oxygenation and nutrition of the various structures of the skin. In particular, at the level of the fibroblasts, it is responsible for the distribution of all the raw materials that are needed to produce the fibers of collagen and elastin. At the same time it drains the waste products produced by their metabolism. The flow of blood supplied to tissue is regulated at both the general organism level and at the local tissue level.

Cutaneous deterioration results from changes to the dermal microvascular system following, in all cases, a reduction in the amount of blood supplied to the skin, via an atrophy of the dermal microcirculatory system.

Furthermore, it has also been shown that absolutes according to the invention can advantageously be used as anti-adipose active ingredients in cosmetic compositions, for the preventive or curative treatment of cellulite and of localized adipose deposits, or in therapeutic compositions for the treatment of obesity.

Known slimming creams currently contain at least one active ingredient promoting lipolysis and/or inhibiting lipogenesis, and/or aim to restore capillary and lymphatic microcirculation. The compositions provided by the invention open up a new direction in the fight against cellulite. Although acting on the traditional targets, like the known slimming creams, the compositions according to the invention operate at the level of the process of differentiation of preadipocytes to mature adipocytes, a key stage in the growth of fat.

In simple terms, cellulite corresponds to the concentration of adipose tissue in certain parts of the body, in particular on the hips, buttocks, knees and forearms. This adipose tissue or fat in the organism is present underneath almost the entire surface of the skin. Cellulite is often associated with global adipose deposits, and the stability of the fat is an important factor in controlling the development of cellulite.

Excessive development of adipose tissue is conventionally linked to an increase in the volume of adipocytes, and in their triglycerides content, without an increase in their number: this is known as hypertrophy. In certain cases of excess weight, hypertrophy is accompanied by hyperplasia, in other words by an increase in the number of adipose cells.

It has now also been shown that the number of fat cells is not determined in the perinatal period, since adipocytes can form throughout life. This process starts with precursor cells known as preadipocytes. The preadipocyte is a thin cell with a fibroblastic morphology: it is this rather than the adipocyte that is capable of multiplying.

In simple terms, terminal adipocytic differentiation takes place in two stages, with conversion of the preadipocyte into a mature adipocyte, the latter being capable of accumulating triglycerides.

The present invention provides active principles, present in *Allium* sativum bulb absolutes, by means of which adipocytic conversion of preadipocytes to mature adipocytes can be inhibited by topical application.

*Allium* sativum absolutes according to the invention thus act on a new aspect of the fight against cellulite: by limiting the recruitment of dormant preadipocytes, they limit the expansion of adipose tissue.

Their effectiveness is not confined to this, however, because it has been found that a single anti-adipose active ingredient according to the invention provides several keys for combating cellulite. This is because an anti-adipose agent according to the invention also provides good vascularization of the adipose tissue.

The absolutes according to the invention are thus highly effective anti-adipose active ingredients which eliminate the need for multiple combinations of active ingredients in cosmetic or therapeutic slimming formulations.

Other experiments have also demonstrated, surprisingly, that the anti-adipose active ingredients according to the invention are also active at the level of mature hypertrophied adipocytes. They thus act on both processes of adipose growth, hyperplasia and hypertrophy, allowing them to be used successfully in the therapeutic domain for the treatment of obesity. Furthermore, these anti-adipose active ingredients act locally on the adipose cell without causing the release into the bloodstream of some of its fatty acids which, having not been burnt, could have a damaging effect on the health (deposition on the arterial wall or on intra-abdominal tissue). Another advantage that has been found of the anti-adipose active ingredients according to the invention lies in the fact that the phenomena obtained are reversible and that as a consequence they do not cause a blockage of the physiological mechanism.

The invention thus provides in general terms a composition containing at least one absolute according to the invention.

The invention also extends to a therapeutic composition, in particular for the topical treatment of cutaneous disorders and/or obesity, containing at least one absolute according to the invention. The invention also extends to a cosmetic composition for the preventive or curative topical treatment of skin disorders and/or cellulite and of localized dermal adipose deposits containing at least one absolute according to the invention. Treatment of localized dermal adipose deposits refers to a treatment of localized fat at the level of both the dermis and the hypodermis.

A composition according to the invention advantageously contains a quantity of at least one absolute according to the invention adjusted so as to at least significantly induce VEGF secretion and/or at least significantly inhibit the differentiation of preadipocytes to mature adipocytes, without significantly causing cutaneous irritation or sensitization.

The quantity of absolute(s) according to the invention is advantageously adjusted so as to at least significantly promote cutaneous microcirculation and/or for the treatment of cellulite and/or of localized adipose deposits. According to the invention this quantity is preferably between 3 ppm and 20 ppm—in particular in the order of 10 ppm.

It should be noted that within the performance of the present invention, although the various absolutes are diluted to 25% in ethanol, the proportion of absolute(s) in ppm in the various compositions according to the invention refers to a quantity of "pure" absolute(s), in other words an absolute containing less than 2% residual ethanol.

According to an embodiment and according to the invention, the composition contains at least one *Allium* sativum bulb absolute in aqueous solution.

According to the invention the composition consists of an aqueous solution of at least one *Allium* sativum bulb absolute.

In a preferred embodiment, a composition according to the invention contains at least one absolute obtained from a concrete extracted from *Allium* sativum bulbs. According to this same embodiment, a composition according to the invention advantageously also contains at least one absolute obtained from an oleoresin extract extracted from *Allium* sativum bulbs.

More particularly, a composition according to the invention is advantageously characterized in that it contains at least one *Allium* sativum bulb absolute chosen from: an absolute obtained from a concrete extracted with hexane; an absolute obtained from a concrete extracted with ethyl acetate; an absolute obtained from an oleoresin extract extracted with acetone.

According to the invention, for a composition containing an absolute obtained from a concrete extracted with hexane, the quantity thereof is advantageously between 3 ppm and 20 ppm—in particular in the order of 10 ppm.

According to the invention, for a composition containing an absolute obtained from a concrete extracted with ethyl acetate or an absolute obtained from an oleoresin extract extracted with acetone, the quantity thereof is advantageously between 5 ppm and 20 ppm—in particular in the order of 10 ppm.

Furthermore, the therapeutic or cosmetic compositions according to the invention represent a skin treatment which is preferably applied as an external treatment to the areas of the skin to be treated at least once a day, every day of the year.

The compositions according to the invention require no active ingredient other than the absolutes according to the invention. The *Allium* sativum absolute(s) can represent the sole microcirculation activating agent(s) or anti-adipose active ingredient(s) in the said composition. That being the case, a composition according to the invention can be free from auxiliary active ingredients. In particular, the *Allium* sativum bulb absolute(s) is/are preferably the only plant extract(s) in a composition according to the invention.

However, a composition according to the invention can also be used for "flash" treatments consisting of a treatment performed over 2 or 3 months, particularly before the summer period. In this case it advantageously contains an auxiliary active ingredient consisting of a lipolytic agent of any type known per se. A composition according to the invention advantageously contains at least one lipolytic agent chosen from lipolytic agents of natural origin (such as caffeine and agents capable of stimulating AMPc synthesis) and synthetic lipolytic agents (xanthic compound(s)).

Other auxiliary active ingredients, in particular having a cosmetic effect, can be used in conjunction with the absolutes according to the invention.

A composition according to the invention can contain a certain number of agents capable of: stabilizing the elastic network (for example silicon derivatives); and/or producing an immediate toning effect (incorporation of synthetic polymers or plant proteins (soybean, wheatgerm); and/or ensuring optimum hydration (incorporation of wetting agents and/or restructuring agents).

A composition according to the invention advantageously does not require the incorporation of agents capable of improving its penetrative power (such as exfoliants).

The composition according to the invention can contain any excipient which is compatible with the absolutes according to the invention, which is pharmaceutically or cosmetically acceptable, and which can contain any appropriate additives, including gelling agents, perfumes, preservatives, stabilizers, colorants, etc., allowing the desired and appropriate galenic form to be obtained.

The composition according to the invention advantageously takes the form of a simple lotion.

The inventor was thus surprised to find that in a composition according to the invention the odor of garlic can more easily be masked than can that of an oleoresin or a concrete produced from the same plant. Until then this result was entirely unforeseeable for the person skilled in the art, since plant absolutes are used principally for their odoriferous property. An absolute according to the invention, however, in addition to displaying advantageous properties for the treatment of cellulite and/or adipose deposits and/or obesity, also has the advantage of being able to be incorporated into compositions of creams or of lotions, of simple manufacture, and of allowing effective treatment by topical application with no unpleasant odor.

Examples of the production of a composition according to the invention are provided below.

For the production of lotions based on garlic absolute, the quantities in concentration by volume of the various constituents can be as follows:

Composition 1:
*Allium* sativum bulb absolute obtained from a concrete extracted with hexane: 0.0003% to 0.002%
Excipient: concentration adjusted to make 100%

Composition 2:
*Allium* sativum bulb absolute obtained from a concrete extracted with ethyl acetate: 0.0005% to 0.002%
Excipient: concentration adjusted to make 100%

Composition 3:
*Allium* sativum bulb absolute obtained from an oleoresin extract extracted with acetone: 0.0005% to 0.002%
Excipient: concentration adjusted to make 100%

A composition according to the invention is extremely simple and inexpensive.

The invention extends to a therapeutic and/or cosmetic, preventive or curative treatment process for cutaneous disorders, for cellulite, for localized dermal adipose deposits or for obesity, wherein at least one *Allium* sativum bulb absolute is applied topically as a microcirculation activating agent and/or as an anti-adipose active ingredient to the areas of skin to be treated. The invention also concerns a treatment process wherein a composition according to the invention is used.

The invention also extends to the use of at least one *Allium* sativum bulb absolute for the preparation of a therapeutic composition, particularly for the topical treatment of skin complaints or of obesity by topical application on the areas of skin to be treated, wherein an effective quantity of at least one *Allium* sativum bulb absolute is incorporated into the composition as a microcirculation activating agent and/or as an anti-adipose agent.

In a process or a use according to the invention a quantity of at least one *Allium* sativum bulb absolute is advantageously used that is adjusted so as to at least significantly induce VEGF secretion or inhibition of the differentiation of preadipocytes to mature adipocytes, without causing cutaneous irritation or sensitization.

In a process or a use according to the invention a composition according to the invention is advantageously applied topically to at least one area of skin to be treated.

The effectiveness of the invention is demonstrated by the results of examples 1 to 6 described below and illustrated by reference to FIGS. 1A to 1F, 2A and 2B, 3A and 3B, appended.

FIGS. 1A to 1F, 2A and 2B are microscopic photographic images of adipose cells. FIGS. 3A and 3B are photographic images of electrophoresis gels.

EXAMPLE 1

Obtaining *Allium* Sativum Bulb Absolutes and Preparing ACH, ACEA and AOA Absolutes and Solutions Incorporating them The absolutes according to the invention are prepared according to a process which in itself is standard, well known and well defined in the perfume industry.

Obtaining an ACH Absolute

A first step involves preparing a concrete of *Allium* sativum bulbs. To this end, peeled cloves of fresh garlic are mechanically ground. Hexane extraction is then performed. The concrete is recovered after total evaporation of the hexane by moderate heating, without bringing the mixture to the boil. This concrete contains the waxes and the aromatic products. At ambient temperature it has a paste-like appearance and is yellow in color.

After dissolving this concrete in ethanol by washing, the solution is filtered and then frozen to −10° C. to eliminate the waxes. After distillation of the ethanol the ACH absolute is obtained. Diluted to 25% in ethanol, it has the appearance of a clear, light yellow solution with a strong odor.

Obtaining the ACEA Absolute

The ACEA is prepared by a method comparable to that for obtaining the ACH, the first step consisting this time of an extraction with ethyl acetate.

The ACEA absolute, diluted to 25% in ethanol, has the appearance of a clear, light brown solution with a moderate odor.

Obtaining the AOA Absolute

The AOA is prepared by a method comparable to that for obtaining the ACH, the first extraction being performed this time from cloves of garlic that have previously undergone a drying stage, and using acetone. At the end of this first extraction, an oleoresin extract is obtained. At ambient temperature it takes the form of a very dark brown colored paste. The AOA absolute is then prepared as indicated above.

This AOA absolute, diluted to 25% in ethanol, has the appearance of a clear brown solution with a very slight odor.

A simple test allowing the absolutes according to the invention to be characterized and to be differentiated from most other garlic-based extracts (oleoresins, concretes, essential oils, aqueous extracts) involves cooling the solution to a very low temperature, in particular of around −20° C. Only the absolutes remain liquid and clear. No fatty deposits are observed.

Preparing Aqueous Solutions of ACH, ACEA and AOA Absolutes

Aqueous solutions of ACH, ACEA and AOA are prepared by diluting, in a ratio of 1/10 in water for cellular culture (Eurobio® France), stock solutions of each absolute (ACH, ACEA or AOA) in a ratio of 18.4 µl of absolute (ACH, ACEA or AOA) and 981.6 µl of water for cellular culture (Eurobio® France).

EXAMPLE 2

Effect of ACH, ACEA and AOA on Primary Cultures of Human Dermal Microvascular Cells At the level of cutaneous microcirculation, the vessels that are present in the skin, principally in the papillary dermis, consist of a layer of endothelial cells, a muscle wall, a discontinuous layer of pericytes, and a basal membrane.

The endothelial cell has important functions that are required in the blood-tissue interface: it plays a dual role by controlling both the state of tension in the vessel, in other words the tissue blood flow, and the structure of the arterial wall. It has secretory and metabolic activities, and it is at the level of these cells that the process of angiogenesis begins, ensuring the formation of new vessels.

Cells and Treatment

Primary cultures of human dermal microvascular cells (p3 HdMEC, Clonetics®) were seeded in 6-well plates (3500 cells/well) and cultivated in complete EBM medium (endothelial basal medium) to which are added aliquots supplied by the supplier (Clonetics®): 10 ng/ml recombinant EGF; 5 µg/ml insulin; 1 µg/ml hydrocortisone; 50 µg/ml gentamicin; 50 ng/ml amphotericin B; and 5% SVF. The experiments were performed between cycles 5 and 7. The HdMEC cells are cultivated in the medium, to which finally 3 to 10 µl of an ACH or ACEA or AOA solution are added per milliliter of culture medium. Control HdMEC cells are kept in culture in the medium alone. The culture medium is renewed every 2 days.

The activity criteria used are:
  stimulation of the differentiation of HdMEC cells. The morphological changes are determined by morphological analysis by inverse phase microscopy coupled to a CCD camera
  stimulation of the secretion of the angiogenic factor VEGF (vascular endothelial growth factor) by analysis of the VEGF secreted in the culture medium (Quantikine Human VEGF Immunoassay, R&D Systems, UK).

Results

Morphological Changes

The addition of ACH or ACEA or AOA to the culture medium for HdMEC cells induces morphological changes: the HdMEC cells lengthen into a spindle shape and expand towards adjacent cells. The majority of the control HdMEC cells take the form of a homogeneous population of polygonal cells, with a central core and indistinct cell borders.

These structural rearrangements lead to the formation of a type of capillary-like network.

VEGF Secretion

The addition of ACH or ACEA or AOA to the culture medium for HdMEC cells very significantly induces the secretion of VEGF in the culture medium. The *Allium sativum* bulb absolute obtained from a concrete extracted with hexane (ACH), the *Allium* sativum bulb absolute obtained from a concrete extracted with ethyl acetate (ACEA), the *Allium* sativum bulb absolute obtained from an oleoresin extract extracted with acetone (AOA), act on the differentiated functions of the endothelial cells, without modifying the proliferative properties. This adjustment of the VEGF rates leads to an increase in cutaneous microvascularization.

EXAMPLE 3

Effect of Solutions of ACH, ACEA or AOA on Adipocyte Morphology (FIGS. 1A to 1F)

Cellular Models and Treatments used

The mechanisms involved in the process of adipocyte differentiation have been studied in vitro for many years (general review: Klaus S., BioEssays, 19:215-223, 1997).

The biological activities of ACH, ACEA and AOA are demonstrated using cultures of 3T3-F442A cells (murine cell line, used for its capacity to accumulate lipids), then confirmed on primary cultures of human preadipocytes.

The cells are seeded in 6-well plates (seeding density: 15000 cells/well) and kept in a DMEM-10% SVD and antibiotics medium to confluence. At confluence, the preadipocytes are then cultivated in a DMEM-10% SVF and insulin medium. The treated cells are kept in the culture medium, to which finally 25 µl of one of the solutions to be tested (ACH or ACEA or AOA) are added per milliliter of culture medium. The control 3T3-F442A preadipocytes are cultivated in the culture medium, to which 25 µl of control solution are added per milliliter of culture medium. The culture medium is renewed every 48 hours.

Primary Cultures of Human Preadipocytes

The human preadipocytes (ZenBio®, USA) are cultivated in accordance with the supplier's instructions. On receipt, the human preadipocytes are cultivated in the appropriate medium supplied, to which finally 3 µl to 10 µl of one of the solutions to be tested (ACH or ACEA or AOA) are added per milliliter of culture medium. The control preadipocytes are kept in culture in the medium alone. The culture medium is renewed every 3 days.

Results

Figure 1B:
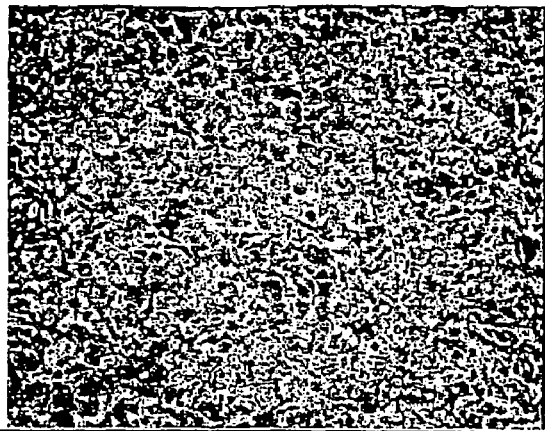
Figure 1C:
Figure 1D:

At the end of 7 days (3T3-F442A cells, FIGS. 1A and 1B) and 9 days (human preadipocytes, FIGS. 1C to 1F) of treatment, the effect of the solutions of ACH, ACEA and AOA on the differentiation process was studied on the basis of morphological criteria, by microscopic observation of the treated cultures and control cultures. The cells are regarded as being differentiated by morphological analysis by inverse phase microscopy coupled to a CCD camera if they acquire a round contour and if their cytoplasm is completely filled with lipid droplets. The solutions of ACH, ACEA or AOA are found to inhibit cellular differentiation in murine 3T3-F442A preadipocytes (FIGS. 1A and 1B).

At the end of 7 days of chronic treatment the ACH solution (FIG. 1A) induces a significant reduction in the number of mature adipocytes developed. The majority of the cells retain their fibroblastic preadipocyte morphology with a very pronounced inhibition of lipid accumulation. Although not shown in the figures, the same results are obtained with the solutions of ACEA and AOA. The control 3T3-F442A cells (FIG. 1B) follow the normal process of terminal differentiation and acquire the morphological characteristics of mature adipocytes, with a cytoplasm filled with droplets of triglycerides, as demonstrated by the high refractive power.

The solutions of ACH, ACEA or AOA are also found to inhibit the process of terminal differentiation of human preadipocytes.

Figure 1E:
Figure 1F:

The human preadipocytes cultivated in the presence of a solution of ACH (FIG. 1C) retain a preadipocyte morphology: the human cells remain spindle-shaped, with very few intra-cytoplasmic lipid droplets detectable. The same results are obtained with the solutions of ACEA (FIG. 1D) and of AOA (FIG. 1E). By comparison, the control human preadipocytes (FIG. 1F) lose their fibroblastic morphology, with the appearance of a spherical shape and the existence of numerous intra-cytoplasmic lipid vesicles identifiable by their high refractive power.

Long-term treatment with the *Allium* sativum bulb absolute obtained from a concrete extracted with hexane (ACH), the *Allium* sativum bulb absolute obtained from a concrete extracted with ethyl acetate (ACEA), the *Allium* sativum bulb absolute obtained from an oleoresin extract extracted with acetone (AOA) limits the morphological and biological changes that are characteristic of adipocyte differentiation. On contact with ACH, ACEA and AOA the preadipocytes are no longer sensitive to the hormonal environment which regulates their lipid metabolism and which normally allows the conversion of preadipocytes into mature differentiated adipose cells.

EXAMPLE 4

Figure 2A:
Figure 2B:
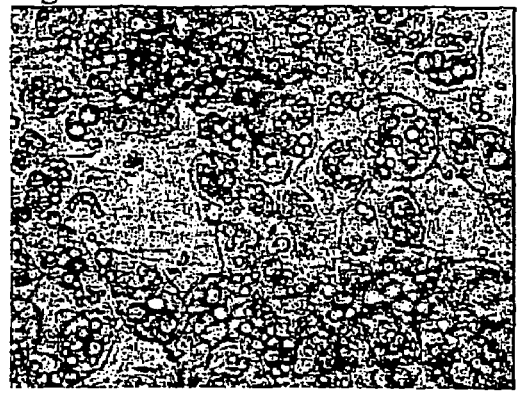
Figure 3A:
Figure 3B:
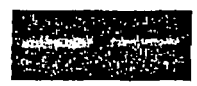

Effect of Solutions of ACH, ACEA or AOA on the Morphology of Mature Hypertrophied Adipocytes (FIGS. 2A and 2B)

At confluence, the 3T3-F442A preadipocytes are cultivated for 4 days in a differentiating medium (DMEM-10% SVF and insulin). Under these conditions the cells change into "mature adipocytes", whose volume and triglycerides content has been increased. The cells are then treated in the same way as before.

In comparison to the control mature adipocytes (FIG. 2B), which have a bulky, spherical shape and a large accumulation of intra-cytoplasmic lipid vesicles, the mature adipocytes treated with a solution of ACH (FIG. 2A) have a less rounded cellular morphology and a greatly reduced content of intra-adipocyte lipid vesicles, such that the solution of ACH according to the invention proves to be effective in the process of restricting adipocyte hypertrophy by reversing the differentiation process. The same results are obtained with the solutions of ACEA or AOA according to the invention.

EXAMPLE 5

Effect of Solutions of ACH, ACEA or AOA on PPARγ2 mRNA expression (FIGS. 3A and 3B)

The differentiation of adipocytes is an important component in the development of adipose tissue and of obesity. The process of adipocyte differentiation is characterized in vitro by the programmed induction of various genes regulating lipoprotein lipolysis, the cell absorption of fatty acids, and the synthesis of fatty acids and triglycerides. In simple terms these genes can be categorized as differentiation markers of the following types: very early (such as lipoprotein lipase mRNA expression), early (such as PPARγ2 mRNA expression) or late (such as leptin expression) (general review: Morrison R. F., Farmer S. R., J. Cell. Biochem Suppl. 32/33: 59–67, 1999). In this way the precise stage of adipocyte differentiation can be established by studying the level of expression of the relevant mRNAs (PPARγ2 mRNA) or by the level of leptin expression.

The process of terminal differentiation is characterized by the induction of early and late differentiation markers (general review: Morrison R. F., Farmer S. R., J. Cell. Biochem Suppl. 32/33:59–67, 1999).

The family of PPAR-type (peroxisomal proliferator-activated receptor) nuclear receptors comprises 3 sub-types: PPARα, PPARδ, PPARγ. PPARα is strongly expressed in the liver, where it regulates the expression of the genes involved in lipid metabolism. PPARδ expression is ubiquitous; the function of this receptor has not yet been determined. PPARγ exists in the form of two isoforms, PPARγ1 and PPARγ2. It is PPARγ2 that is strongly expressed in the adipose tissue of mammals. When PPARγ2 is activated it induces the transcription of several adipocyte genes that code for proteins and enzymes involved in creating and maintaining the adipocyte phenotype. It therefore plays a major role in the differentiation and metabolism of adipose cells.

The effect on PPARγ2 mRNA expression of solutions of ACH, ACEA or AOA was determined at the end of 3 days (FIG. 3A, 3T3-F442A cells) or 6 days (FIG. 3B, human preadipocytes) of treatment. The PPARγ2 mRNA content is analyzed by RT-PCR (reverse transcription-polymerase chain reaction) after first purifying the RNA in accordance with the procedure for the RNeasy Total RNA System kit (Qiagen®), quantifying the RNA content in samples by measuring and recording the absorption coefficients at 260 and 280 nm, and verifying the quality of the RNAs obtained after migration onto agarose gel.

For the RT stage, complementary DNA (cDNA) is synthesized from 1 μg of total RNA (3T3-F442A) or from 0.2 μg of total RNA (human preadipocytes). The amplifications of cDNA that code for PPARγ2 are obtained in the presence of appropriate Sens and Anti-sens primers (Genset®, cf. Table 1). The sizes of the PCR products are 307 base pairs (3T3-F442A cells) and 582 base pairs (human preadipocytes). Appropriate controls (reverse transcription and PCR amplification stages) were performed. The PCR mixtures underwent 22 cycles (3T3-F442A cells) or 35 cycles (human preadipocytes) of amplification by denaturation (2 minutes at 94° C.), hybridization (1 minute at 60° C.) and elongation (6 minutes at 72° C.). The PCR products are analyzed by electrophoresis in agarose gel and displayed with ethidium bromide.

The level of expression of the adipogenic transcription factor PPARγ2 is greatly reduced when the 3T3-F442A cells have been in contact with a solution of ACH (FIG. 3A, result 2) in comparison to the control cells, as demonstrated by the intensity of the band (FIG. 3A, result 1). The same results are obtained with the solution of ACEA (FIG. 3A, result 3) and the solution of AOA (FIG. 3A, result 4).

Likewise, the solutions of ACH, ACEA or AOA according to the invention significantly inhibit the PPARγ2 mRNA expression of human preadipocytes (FIG. 3B, result 6 illustrating a treatment with a solution of ACH) in comparison to the control human preadipocytes (FIG. 3B, result 5).

The *Allium* sativum bulb absolute obtained from a concrete extracted with hexane (ACH), the *Allium* sativum bulb absolute obtained from a concrete extracted with ethyl acetate (ACEA) and the *Allium* sativum bulb absolute obtained from an oleoresin extract extracted with acetone (AOA) act at the level of the differentiation program by reducing the expression of the PPARγ2 messenger.

EXAMPLE 6

Effect of ACH, ACEA and AOA Absolutes on Leptin Secretion

The capacity of the ACH, ACEA and AOA absolutes to inhibit the differentiation process in human preadipocytes was determined by quantitative measurement of the rates of leptin secreted in the culture medium of the various assays. Leptin, coded by the ob gene and synthesized and secreted by adipocytes, is regarded as a late marker of the adipocyte differentiation process. In vitro, the basal secretion of leptin gradually increases throughout the process of conversion of preadipocytes to mature adipocytes (MacDougald, O. A. et al., Proc Natl Acad Sci, USA, 92:9034–9037, 1995).

The effect on leptin secretion of the ACH, ACEA and AOA absolutes was studied over a treatment period of 9 days (human preadipocytes). The rates of leptin secreted by the control cells and by the treated cells were measured in the various culture media, sampled at 3, 6 and 9 days (days on which the medium was renewed). The rates of leptin released were determined quantitatively by ELISA analysis (R&D Systems Europe) in accordance with the supplier's instructions. The results are expressed as the mean±standard deviation from the mean. The statistical comparisons are performed using Student's T test ($p<0.005$ representing the significance level).

The results are standardized as follows: at the end of the 9 days of treatment the leptin values measured for each of the treatments on day 3, day 6 and day 9 are cumulated and expressed as a percentage of the values obtained for the controls (Table 2).

TABLE 1

|  | Murine PPARγ2 | Human PPARγ2 |
|---|---|---|
| Sens | 5'-TGTTGACCCAGAGCATGGTGCCT-3' | 5'-GCGATTCCTTCACTGATAC-3' |
| Anti-sens | 5'-CAGGTTCTACTTTGATCGCACTT-3' | 5'-GCATTATGAGACATCCCCAC-3' |

TABLE 2

Effect of ACH, ACEA or AOA on leptin secretion

| Treatment | Concentration | Leptin (%) | | |
|---|---|---|---|---|
| | | Mean | Standard deviation from mean | Significance |
| ACH | 3 ppm | 69.4 | 4.4 | $P < 0.01$ |
| ACH | 10 ppm | 36.3 | 0.1 | $P < 0.001$ |
| ACEA | 10 ppm | 81.7 | 2.1 | $P < 0.01$ |
| AOA | 10 ppm | 80.9 | 2.1 | $P < 0.001$ |

The human preadipocytes cultivated in the presence of ACH, ACEA and AOA absolute secrete in the culture medium quantities of leptin that are significantly lower than those detected in the culture medium of untreated control human preadipocytes. The results obtained show that the absolutes of ACH, ACEA or AOA act at the level of the differentiation program and are capable of inhibiting the process of adipocyte conversion.

The invention claimed is:

1. An *Allium sativum* bulb absolute, which is prepared by extracting *Allium sativum* bulbs with a volatile, non-aqueous extraction solvent to produce a concrete or oleoresin; and extracting the concrete or oleoresin with ethanol.

2. The *Allium sativum* bulb absolute as claimed in claim 1, wherein the concrete of *Allium sativum* bulbs is extracted with ethanol.

3. The *Allium sativum* bulb absolute as claimed in claim 1, wherein the volatile, non-aqueous extraction solvent is hexane.

4. The *Allium sativum* bulb absolute as claimed in claim 1, wherein the volatile, non-aqueous extraction solvent is ethyl acetate.

5. The *Allium sativum* bulb absolute as claimed in claim 1, wherein the volatile, non-aqueous extraction solvent is acetone.

6. A composition containing the *Allium sativum* bulb absolute, according to claim 1, wherein the composition is free from waxes.

7. The composition as claimed in claim 1, wherein said composition comprises an aqueous solution.

8. The composition as claimed in claim 1, wherein said composition consists of an aqueous solution.

9. The composition as claimed in claim 1, wherein said composition contains an effective amount of said *Allium sativum* bulb absolute so as to at least induce VEGF secretion.

10. The composition as claimed in claim 6, wherein said composition contains an effective amount of said *Allium sativum* bulb absolute so as to at least promote cutaneous microcirculation.

11. The composition as claimed in claim 6, wherein said composition contains an effective amount of said *Allium sativum* bulb absolute so as to at least inhibit the differentiation of preadipocytes to mature adipocytes.

12. The composition as claimed in claim 6, wherein said composition contains an effective amount of said *Allium sativum* bulb absolute for topical treatment of cellulite and/or of localized dermal adipose deposits.

13. The composition as claimed in claim 6, wherein said composition contains between 3 ppm and 20 ppm of said *Allium sativum* bulb absolute.

14. The composition as claimed in claim 6, wherein the *Allium sativum* bulb absolute is extracted from an *Allium sativum* concrete.

15. The composition as claimed in claim 6, wherein said composition also contains at least one absolute obtained from an *Allium sativum* oleoresin.

16. The composition as claimed in claim 6, wherein the *Allium sativum* bulb absolute said composition is chosen from an absolute obtained from a concrete prepared with hexane; an absolute obtained from a concrete prepared with ethyl acetate; an absolute obtained from an oleoresin extract prepared with acetone, or mixtures thereof.

17. A cosmetic skin treatment process comprising the step of applying an effective amount of the *Allium ativum* bulb absolute according to any one of claims 1–6.

18. A cosmetic skin treatment process comprising the step of applying a composition as claimed in claim 1 topically to at least one area of skin to be treated.

19. A process of treating obesity comprising topically applying an effective amount of the *Allium sativum* bulb absolute according to claim 1.

20. A process for obtaining an *Allium sativum* bulb absolute comprising the following steps;

extraction of *Allium sativum* bulb with a volatile non-aqueous solvent, evaporation of the solvent to obtain a first extraction product, wherein the first extraction product undergoes a subsequent extraction with ethanol to obtain an absolute.

21. The process as claimed in claim 20, wherein the subsequent extraction with ethanol consists of:

dissolving the first extraction product in ethanol at ambient temperature and recovering a first ethanol solution by filtration, cooling the first ethanol solution to a temperature in the order of −10°C. and then filtering it to recover a second ethanol solution, distilling the ethanol from the second ethanol solution to finally obtain an absolute.

22. The process as claimed in claim 21, wherein the extraction step with a volatile non-aqueous solvent is performed with a volatile non-aqueous and non-aromatic solvent.

* * * * *